US012630634B2

(12) United States Patent
Danger et al.

(10) Patent No.: US 12,630,634 B2
(45) Date of Patent: May 19, 2026

(54) RECOMBINANT FULL-LENGTH SINGLE CHAIN IMMUNOGLOBULINS

(71) Applicant: ETABLISSEMENT FRANCAIS DU SANG, Saint Denis (FR)

(72) Inventors: Yannic Danger, Saint Denis (FR); Michel Cogne, Saint Denis (FR)

(73) Assignee: ETABLISSEMENT FRANCAIS DU SANG, Saint Denis (FR)

( * ) Notice: Subject to any disclaimer, the term of this patent is extended or adjusted under 35 U.S.C. 154(b) by 1081 days.

(21) Appl. No.: 16/977,825

(22) PCT Filed: Mar. 5, 2019

(86) PCT No.: PCT/EP2019/055453
§ 371 (c)(1),
(2) Date: Sep. 3, 2020

(87) PCT Pub. No.: WO2019/170677
PCT Pub. Date: Sep. 12, 2019

(65) Prior Publication Data
US 2021/0024632 A1     Jan. 28, 2021

(30) Foreign Application Priority Data

Mar. 5, 2018    (EP) ..................................... 18305232
Jul. 16, 2018    (EP) ..................................... 18183739

(51) Int. Cl.
*C07K 16/28*      (2006.01)
*C12N 15/861*      (2006.01)
*G01N 33/541*      (2006.01)

(52) U.S. Cl.
CPC ........ *C07K 16/2818* (2013.01); *C12N 15/861* (2013.01); *G01N 33/541* (2013.01); *C07K 2317/50* (2013.01)

(58) Field of Classification Search
None
See application file for complete search history.

(56) References Cited

U.S. PATENT DOCUMENTS

| | | | |
|---|---|---|---|
| 2006/0156422 A1* | 7/2006 | Dalrymple | ......... A01K 67/0271 800/18 |
| 2014/0072581 A1* | 3/2014 | Dixit | .................. C07K 16/2809 435/69.6 |
| 2015/0087021 A1* | 3/2015 | Kochanek | .............. C12N 15/85 435/325 |
| 2016/0222130 A1 | 8/2016 | Kamohara et al. | |

FOREIGN PATENT DOCUMENTS

| | | |
|---|---|---|
| EP | 2 050 764 | 4/2009 |
| WO | WO 2014/018572 | 1/2014 |
| WO | WO 2017/005923 | 1/2017 |
| WO | WO 2018/017863 | 1/2018 |
| WO | WO 2018/148447 | 8/2018 |

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Poosarla et al., Biotechn. Bioeng., 114(6): 1331-1342 (Year: 2017).*
Gu et al., Ann Biomed Eng 38(2): 537-549 (Year: 2010).*
Written Opinion in International Application No. PCT/EP2019/ 055453, Apr. 9, 2019, pp. 1-6.

* cited by examiner

*Primary Examiner* — Phuong Huynh
(74) *Attorney, Agent, or Firm* — SALIWANCHIK, LLOYD & EISENSCHENK

(57) ABSTRACT
The present invention relates to an antibody comprising an immunoglobulin heavy chain variable region (VH), an immunoglobulin light chain variable region (VL), an immunoglobulin light chain constant region (CL), an immunoglobulin heavy chain constant region (CH), and two sequences encoding peptide linkers (PL1 and PL2), wherein VH is fused to VL through PL1 and CL is fused to CH through PL2, and its uses for therapeutic or diagnostic purposes. The invention further relates to a recombinant nucleic acid molecule encoding said antibody, and an expression cassette, vector, viral particle, host cell, transgenic organism or pharmaceutical composition comprising said recombinant nucleic acid molecule.

10 Claims, 3 Drawing Sheets

Specification includes a Sequence Listing.

Full-Ig produced in 293    Full-Ig produced in CHO

Irrelevant mAb

RECOMBINANT FULL-LENGTH SINGLE CHAIN IMMUNOGLOBULINS

CROSS-REFERENCE TO RELATED APPLICATION

This application is the U.S. national stage application of International Patent Application No. PCT/EP2019/055453, filed Mar. 5, 2019.

The Sequence Listing for this application is labeled "Seq-List.txt" which was created on Jul. 31, 2020 and is 2 KB. The entire content of the sequence listing is incorporated herein by reference in its entirety.

FIELD OF THE INVENTION

The present invention relates to the field of medicine, in particular to a new structure of immunoglobulins that can break the locks to re-engineer on-purpose B-cell specificity.

BACKGROUND OF THE INVENTION

Cancer therapy is a very active field with multiple developments in terms of both immunotherapy, cell therapy and gene therapy. Antibodies targeting tumor-specific antigens or immune checkpoints have completely changed the prognosis of many tumor types, yielding long-term remission and eventually turning fatal diseases into chronic diseases almost under control by the immune system.

While antibody molecules have thus became major tools against cancer, the cells producing these drugs still remain non accessible to biotechnological manipulation and usage for cell therapy. A few reports have preliminary obtained production of recombinant proteins (notably coagulation factors) by plasma cells, but only for short-terms and in experimental settings (Hung et al., 2018. Mol. Ther. J. Am. Soc. Gene Ther., 26, 456-467; Levy et al. 2016. J. Thromb. Haemost. JTH, 14, 2478-2492). Although it would obviously be of high interest to re-engineer on-purpose B-cell specificity and generate tumor-specific B-cells, this is hampered by two biochemical locks.

Firstly, immunoglobulins are H-L polymers needing stoichiometric expression and needing that two recombinant proteins are simultaneously expressed for correct Ig production. Secondly, B cells strongly express high amounts of endogenous Ig. Thus, simple addition (and eventually poor expression) of additional donor (d) Hd and Ld chains, in a recipient (r) cell already expressing Hr and Lr molecules results in a mixture of hybrid molecules (HrLr, HrLd, HdLr and HdLd . . . ) among which the amount of correctly assembled HL chains with the desired donor-like specificity is quite unpredictable.

SUMMARY OF THE INVENTION

In a first aspect, the present invention relates to a recombinant nucleic acid molecule comprising

- a sequence encoding an immunoglobulin heavy chain variable region ($V_H$),
- a sequence encoding an immunoglobulin light chain variable region ($V_L$),
- a sequence encoding a light chain constant region ($C_L$),
- two sequences encoding peptide linkers (PL1 and PL2), and wherein the nucleic acid molecule comprises the following structure:

$$V_H\text{-PL1-}V_L\text{-}C_L\text{-PL2,}$$

wherein PL1 and PL2 are identical or different.

The recombinant nucleic acid molecule may further comprise a donor splice site and exhibit the following structure $V_H$-PL1-$V_L$-$C_L$-PL2-donor splice site Alternatively, the recombinant nucleic acid molecule may comprise

- a sequence encoding an immunoglobulin heavy chain variable region ($V_H$),
- a sequence encoding an immunoglobulin light chain variable region ($V_L$),
- a sequence encoding a light chain constant region ($C_L$),
- a sequence encoding an immunoglobulin heavy chain constant region ($C_H$), and
- two sequences encoding peptide linkers (PL1 and PL2), wherein the nucleic acid molecule comprises the following structure:

$$V_H\text{-PL1-}V_L\text{-}C_L\text{-PL2-}C_H$$

wherein PL1 and PL2 are identical or different.

Preferably, the sequence encoding an immunoglobulin heavy chain constant region encodes three or four immunoglobulin heavy chain constant domains.

The recombinant nucleic acid molecule may further comprise additional polynucleotides for directing integration of said nucleic acid molecule by homologous recombination at a precise location into a genome of a host cell, preferably into an immunoglobulin heavy locus, more preferably between the joining region (JH) genes and the constant region ($C_H$) genes of immunoglobulin heavy chains.

Preferably, the donor splice site is a donor splice site for junction with a CH1 domain of constant immunoglobulin heavy genes.

Preferably, the peptide linkers are from 10 to 25 amino acid length, preferably from 15 to 20 amino acid length.

In another aspect, the present invention relates to an expression cassette comprising a recombinant nucleic acid molecule of the invention operably linked to one or more control sequences that direct the expression of said nucleic acid in a suitable host cell under conditions compatible with the control sequences.

In particular, the recombinant nucleic acid molecule may be operably linked to an immunoglobulin $V_H$ promoter.

In another aspect, the present invention relates to a vector comprising an expression cassette of the invention.

The vector is preferably a viral vector, more preferably a retroviral vector, and even more preferably a lentiviral vector.

In preferred embodiments, said vector is an adeno-associated viral (AAV) vector, preferably AAV6 vector.

In another aspect, the present invention relates to a viral particle comprising a vector of the invention.

In a further aspect, the present invention relates to an isolated cell comprising a recombinant nucleic acid molecule, an expression cassette, a vector or a viral particle of the invention.

Preferably, the cell is a mouse embryonic stem cell.

Alternatively, the cell is B cell, preferably human B cell.

In a further aspect, the present invention relates to a transgenic organism, excepted humans, comprising at least one cell of the invention, preferably said transgenic organism being a mouse.

In another aspect, the present invention relates to an antibody comprising

- an immunoglobulin heavy chain variable region ($V_H$),
- an immunoglobulin light chain variable region ($V_L$),
- an immunoglobulin light chain constant region ($C_L$),
- an immunoglobulin heavy chain constant region ($C_H$), and

3 two sequences encoding peptide linkers (PL1 and PL2), wherein $V_H$ is fused to $V_L$ through PL1 and $C_L$ is fused to $C_H$ through PL2, and wherein PL1 and PL2 are identical or different.

The present invention also relates to a method of producing an antibody of the invention, comprising providing a cell or a transgenic organism of the invention, said cell or organism expressing said antibody, and recovering said antibody from the cell culture or from a sample of said organism.

In a further aspect, the present invention also relates to a pharmaceutical composition comprising a recombinant nucleic acid molecule, an expression cassette, a vector, a viral particle, a cell or an antibody of the invention, and a pharmaceutically acceptable excipient.

DETAILED DESCRIPTION OF THE INVENTION

The inventors herein provide a strategy to break the locks to re-engineer on-purpose B-cell specificity, in particular with an immunoglobulin form suitable for single-chain expression either as a membrane-linked B-cell receptor (BCR) for antigen, or as a secreted antibody. Indeed, they demonstrated that a recombinant full length immunoglobulin may be expressed as a single chain molecule including two linkers and highly similar in structure to a normal and complete immunoglobulin. This molecule was obtained by

Figure 1:
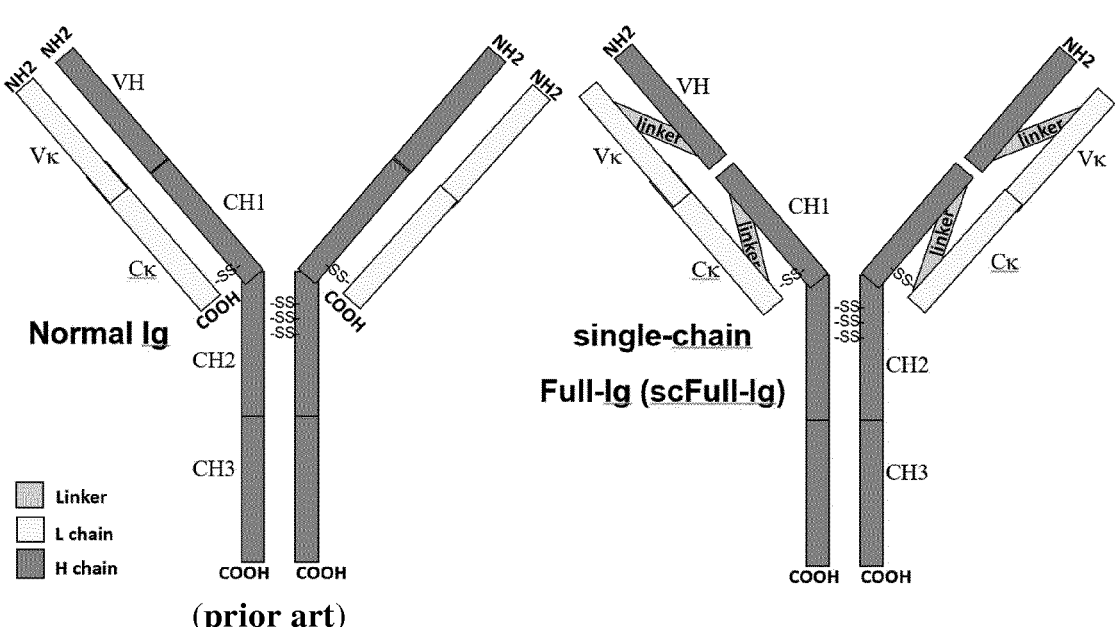
FIG. 1: Schematic representation of an immunoglobulin G1 class (left, prior art) and a full length single chain Ig G1 type of the invention (right). Compared to a natural IgG1, heavy variable domain is linked to the light variable domain by a peptide linker, from the C terminus of the heavy variable domain to the N-terminus of the light variable domain. C-terminus part of the light constant domain is attached to the N-terminus heavy constant domain by another peptide linker.

4 the fusion of all domains of an antibody thanks to the use of at least two peptide linkers, a first linker fusing the C terminus of the heavy variable region to the N terminus of light variable region and a second linker fusing the C terminus of the light constant region to the N-terminal part of the γ heavy constant region CH1 domain (FIG. 1). As shown in the experimental section of this application, the inventors demonstrated that CHO and HEK 293 cells transformed with a nucleic acid encoding said full length single chain immunoglobulin could efficiently produce the recombinant antibody and that this antibody could efficiently recognize its antigen.

This strategy not only solves the problem regarding stoichiometry between heavy and light chains, but also makes it possible to easily interrupt endogenous immunoglobulin heavy chain expression, to promote high expression of the recombinant antibody and to potentially use endogenous regulatory sequences that control alternate splicing and polyadenylation of membrane-type and secreted-type Ig so that the recombinant antibody can be expressed either as a membrane bound BCR in memory B-lymphocytes or as a secreted Ig in plasma cells.

Accordingly, in a first aspect, the present invention relates to a recombinant nucleic acid molecule comprising, or consisting of, a sequence encoding an immunoglobulin heavy chain variable region ($V_H$), a sequence encoding an immunoglobulin light chain variable region ($V_L$), a sequence encoding a light chain constant region ($C_L$), two sequences encoding peptide linkers (PL1 and PL2), and wherein the nucleic acid molecule comprises the following structure:

$V_H$-PL1-$V_L$-$C_L$-PL2.

Preferably, the structure $V_H$-PL1-$V_L$-$C_L$-PL2 means that every of these elements is immediately adjacent to its neighbor(s), i.e. the sequence encoding $V_H$ is directly linked to the sequence encoding PL1, the sequence encoding PL1 is directly linked to the sequence encoding $V_L$, the sequence encoding $V_L$ is directly linked to the sequence encoding $C_L$ and the sequence encoding $C_L$ is directly linked to the sequence encoding PL2.

As used herein, the terms "nucleic acid molecule", "nucleic acid" and "polynucleotide" are used interchangeably and refer to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—$NH_2$) or a mixed phosphoramidate-phosphodiester oligomer. The nucleic acid of the invention can be prepared by any method known to one skilled in the art, including chemical synthesis, recombination, and mutagenesis. In preferred embodiments, the nucleic acid of the invention is a DNA molecule, preferably double stranded DNA molecule, which can be synthesized by recombinant methods well known to those skilled in the art.

A "recombinant nucleic acid" designates a nucleic acid which has been engineered and is not found as such in natural environment and in particular in wild type organisms.

The nucleic acid molecule of the invention comprises a sequence encoding an immunoglobulin heavy chain variable region ($V_H$) and a sequence encoding an immunoglobulin light chain variable region ($V_L$).

The "variable region" or "variable domain" of an antibody refers to the amino-terminal domains of the heavy or light chain of the antibody. The term "immunoglobulin heavy chain variable region" or "variable domain of the heavy chain" may be referred to as "$V_H$". The term "immunoglobulin light chain variable region" or "variable domain of the light chain" may be referred to as "$V_L$". These domains are generally the most variable parts of an antibody and contain the antigen-binding sites.

A light or heavy chain variable region ($V_L$ or $V_H$) consists of a framework interrupted by three hypervariable regions referred to as "complementarily determining regions" or "CDRs". $V_L$ or $V_H$ then generally comprises four framework regions or "FR", which are referred to in the art as "Framework region 1" or "FR1"; as "Framework region 2" or "FR2"; as "Framework region 3" or "FR3"; and as "Framework region 4" or "FR4", respectively. These framework regions and complementary determining regions are preferably operably linked in the following order: FR1-CDR1-FR2-CDR2-FR3-CDR3-FR4 (from amino terminus to carboxy terminus).

The extent of the framework region and CDRs have been precisely defined, for example as in Kabat (see "Sequences of Proteins of Immunological Interest," E. Kabat et al., U.S. Department of Health and Human Services, (1983)). The CDRs of a given VH or VL can be determined by any method available to those skilled in the art. For example, and in a non-limiting manner, the Chlothia or the Kabat method can be used to determine the CDRs (Chothia et al., Nature 342, 877-883; Kabat et al., 1991, Sequences of Proteins of Immunological Interest, 5th Ed., United States Public Health Service, National Institutes of Health, Bethesda). Alternative method of determining CDRs can also be used such as the intermediate method between Chlothia and Kabat called AbM (Oxford Molecular AbM antibody modeling software) or the so-called "Contact" method based on an analysis of available complex structures.

The framework region of an antibody, that is the combined framework regions of the constituent light and heavy chains, serves to position and align the CDRs, which are primarily responsible for binding to an antigen.

The nucleic acid molecule of the invention comprises a sequence encoding a light chain constant region ($C_L$).

By "constant region" as defined herein is meant an antibody-derived constant region that is encoded by one of the light or heavy chain immunoglobulin constant region genes.

By "immunoglobulin light chain constant region", "constant light chain" or "light chain constant region" as used herein is meant the region of an antibody encoded by the kappa (Ckappa) or lambda (Clambda) light chains and may be referred to as "$C_L$". The constant light chain typically comprises a single domain.

In some embodiments, the nucleic acid molecule of the invention comprises, or consists of,
    a sequence encoding an immunoglobulin heavy chain variable region ($V_H$),
    a sequence encoding an immunoglobulin light chain variable region ($V_L$), a sequence encoding a light chain constant region ($C_L$),
    a sequence encoding an immunoglobulin heavy chain constant region ($C_H$), and
    two sequences encoding peptide linkers (PL1 and PL2), and
    wherein the nucleic acid molecule comprises the following structure:

$$V_H\text{-PL1-}V_L\text{-}C_L\text{-PL2-}C_H$$

Preferably, the sequence encoding PL2 is directly linked to the sequence encoding $C_H$.

By "immunoglobulin heavy chain constant region", "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. This region may be referred to as "$C_H$".

The constant heavy chain typically comprises three or four domains. As illustration, for full length IgD, IgG or IgA antibodies, the constant heavy region, as defined herein, refers to the N-terminus of the CH1 domain to the C-terminus of the CH3 domain, and for full length IgE or IgM antibodies, the constant heavy region, as defined herein, refers to the N-terminus of the CH1 domain to the C-terminus of the CH4 domain.

Alternatively, the $C_H$ region may comprise, or consist of, a fragment of the constant heavy chain of a full length antibody. For example, the $C_H$ region may comprise, consist of, one or two domains such as CH1 and/or CH2.

In some other embodiments, the nucleic acid molecule of the invention comprises, or consists of,
    a sequence encoding an immunoglobulin heavy chain variable region ($V_H$),
    a sequence encoding an immunoglobulin light chain variable region ($V_L$),
    a sequence encoding a light chain constant region ($C_L$),
    two sequences encoding peptide linkers (PL1 and PL2), and
    a donor splice site
    wherein the nucleic acid molecule comprises the following structure:

$$V_H\text{-PL1-}V_L\text{-}C_L\text{-PL2-donor splice site}$$

Preferably, the sequence encoding PL2 is directly linked to the sequence comprising the donor splice site.

The donor splice site is designed depending on the host cell contemplated for the expression of the nucleic acid of the invention and the envisaged integration site.

The donor splice site is preferably designed for junction with a CH1 domain of constant immunoglobulin heavy chain genes of a host cell. The use of such donor splice site is illustrated in the articles of Delpy et al. (Eur. J. Immunol., 2003, 33, 2108-2113) or Casola et al. (Nat. Immunol., 2004, 5, 317-327).

Numerous bioinformatics tools are known by the skilled person and may be used to predict and design splicing signals and splicing events such as GeneSplicer (ccb.jh-u.edu/software/genesplicer/) or Spliceport (spliceport.cbcb.umd.edu/). See also Breathnach R, Chambon P. Annu Rev Biochem. 1981; 50:349-83. In one embodiment, the donor splice site is a cryptic splice site.

The nucleic acid molecule of the invention comprises at least two sequences encoding peptide linkers, i.e. PL1 and PL2.

The peptide linkers PL1 and PL2 may be identical or different.

In the antibody encoded by the nucleic acid molecule of the present invention, the peptide linker PL1 joins the C-terminus of the $V_H$ region to the N-terminus of the $V_L$ region, and the peptide linker PL2 joins the C-terminus of the $C_L$ region to the N-terminus of the $C_H$ region.

In the nucleic acid molecule of the invention, the sequence encoding the peptide linker PL1 joins the sequence encoding the $V_H$ region to the sequence encoding the $V_L$ region.

Depending on the embodiments, the sequence encoding the peptide linker PL2 joins the sequence encoding the $C_L$ region to the sequence encoding the $C_H$ region or to a sequence comprising a donor splice site.

Peptide linkers typically vary from 5 to 50 amino acids in length. Preferably, the peptide linkers are from 10 to 25 amino acid length, more preferably from 15 to 20 amino acid length, and even more preferably of about 18 amino acid length.

Typically, the sequence of the peptide linkers comprises a majority of hydrophilic amino acids, or consists of hydrophilic amino acids, such as glycine and serine.

Peptide linkers useful in the invention can be selected by the skilled person from any peptide linkers previously described in single-chain fragment variable (scFv) antibodies. Examples of such peptide linkers are described in Gu et al. (Ann Biomed Eng. 2010 February; 38(2):537-49), Völkel et al. (Protein Eng. 2001 October; 14(10):815-23), Pantoliano et al., (Biochemistry. 1991 Oct. 22; 30(42):10117-25), Whitlow et al., (Protein Eng. 1993 November; 6(8):989-95) or Hennecke et al., (Protein Eng. 1998 May; 11(5):405-10).

Particular examples of such peptide linkers are presented below:

| Name | Sequence | Reference |
|---|---|---|
| PT1 | GGGSAAA (SEQ ID NO: 2) | Gu et al., 2010 |
| PT2 | (GGGGS)$_2$ (SEQ ID NO: 3) | Gu et al., 2010 |
| PT3 | (GGGGS)$_3$ (SEQ ID NO: 4) | Gu et al., 2010 |
| L205 | SSADDAKKDA(AKKDD)$_2$AKKDG (SEQ ID NO: 5) | Pantoliano et al., 1991 |
| L218 | GSTSGSGKPGSGEGSTKG (SEQ ID NO: 1) | Whitlow et al., 1993 |
| LLB18 | SPNGASHSSSASQTGSASGSQ (SEQ ID NO: 6) | Hennecke et al., 1998 |
| Linker-M | GGGGSGGRASGGGGS (SEQ ID NO: 7) | Volkel etal., 2001 |

In a particular embodiment, PL1 and/or PL2 comprise, or consist of, a sequence selected from the group consisting of sequences SEQ ID NO: 1 to 7, and sequences having at least 80%, preferably at least 90%, more preferably at least 91%, 92%, 93%, 94%, 95%, 96%, 97%, 98% or 99%, sequence identity with a sequence of SEQ ID NO: 1 to 7.

In a particular embodiment, PL1 and/or PL2 comprise, or consist of, the sequence GSTSGSGKPGSGEGSTKG (SEQ ID NO: 1), or a sequence having at least 80%, preferably at least 90%, more preferably at least 91%, 92%, 93%, 94%, 95%, 96%, 97%, 98% or 99%, sequence identity with SEQ ID NO: 1.

As used herein, the term "sequence identity" or "identity" refers to the number (%) of matches (identical amino acid residues) in positions from an alignment of two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithms (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as blast.ncbi.nlm.nih.gov/ or see Worldwide Website: ebi-.ac.uk/Tools/emboss/). Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

The recombinant nucleic acid molecule of the invention may further comprise additional sequences for directing integration of said nucleic acid molecule by homologous recombination at a precise location into a genome of a host cell.

Preferably, the nucleic acid molecule of the invention is flanked on both ends by sequences homologous to a precise location of a genome of a host cell. Such sequences can be easily defined by the skilled person.

Homologous recombination may be performed with or without the help of nucleases routinely used for such recombination such as ZFNs, TALE nucleases, CRISPR/Cas9.

In particular, the additional sequences may be microhomology sequences striding over the double strand break (DSB) point created by CRISPR/Cas9 system. Microhomology sequences feature short (usually about 10 to 50 bp) sequences highly specific for a given gene and not found in another location of the targeted genome. Numerous bioinformatics tool are known by the skilled person and may be used to design such sequences such as NBRP Medaka (viewer.shigen.info/cgi-bin/crispr/crispr.cgi). Optionally, these microhomology sequences may be flanked by PITCh binding site to use MMEJ (microhomology-mediated end-joining) mechanism for integration (Sakuma et al., Nat Protoc. 2016 January; 11 (1): 118-33).

In preferred embodiments, these additional sequences allow integration by homologous recombination into an immunoglobulin heavy chain locus, more preferably between the joining region (JH) genes and the constant region ($C_H$) genes of immunoglobulin heavy chains. Preferably, in this embodiment, the nucleic acid molecule of the invention exhibits the following structure $V_H$-PL1-$V_L$-$C_L$-PL2-donor splice site as defined above and RNA splicing leads to a fusion protein comprising $V_H$-PL1-$V_L$-$C_L$-PL2-$C_H$ wherein $C_H$ is encoded by the host cell genome. The insertion site, the sequence of which is used for designing homology sequences, may then be chosen upstream of any $C_H1$ exon from any Ig heavy chain gene.

In another aspect, the present invention relates to an expression cassette comprising a recombinant nucleic acid molecule of the invention operably linked to one or more control sequences that direct the expression of said nucleic acid in a suitable host cell under conditions compatible with the control sequences.

The term "control sequences" means nucleic acid sequences necessary for expression of a gene. Control sequences may be native (operably linked to the coding sequence in a naturally occurring genome) or heterologous (different from the control sequences operably linked to the coding sequence in a naturally occurring genome). Such control sequences include, but are not limited to, a leader, polyadenylation sequence, promoter, signal peptide sequence, and transcription terminator.

As used herein, the term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter.

As used herein, the term "expression cassette" refers to a nucleic acid construct comprising a coding sequence and one or more control sequences required for expression of said coding sequence. Generally, the expression cassette comprises a coding sequence and regulatory sequences preceding (5' non-coding sequences) and following (3' non-coding sequences) the coding sequence that are required for expression of the gene product of interest. Thus, an expression cassette typically comprises a promoter sequence, a 5' untranslated region, a coding sequence and a 3' untranslated region that usually contains a polyadenylation site and/or transcription terminator. The expression cassette may also comprise additional regulatory elements such as, for example, enhancer sequences, a polylinker sequence facilitating the insertion of a DNA fragment within a vector and/or splicing signal sequences. The expression cassette is usually included within a vector, to facilitate cloning and transformation.

In a particular embodiment, the recombinant nucleic acid of the invention is operably linked to an immunoglobulin $V_H$ promoter, preferably an immunoglobulin $V_H$ promoter of the contemplated host cell. Such promoter can be easily selected by the skilled person. Preferably, the contemplated host cell is a human host cell and the promoter is a human promoter, preferably a human immunoglobulin $V_H$ promoter, or any promoter active in the B-cell lineage.

In preferred embodiments, the promoter is an inducible promoter. With this promoter, it is possible to trigger recombinant single-chain antibody production on purpose.

The expression cassette of the invention may further comprise additional sequences for directing its integration by homologous recombination at a precise location into a genome of a host cell. These sequences may be as defined above for the recombinant nucleic acid molecule.

All the embodiments of the recombinant nucleic acid molecule are also contemplated in this aspect.

In another aspect, the present invention relates a vector comprising a recombinant nucleic acid molecule or an expression cassette of the invention.

By "vector" is meant a nucleic acid molecule, preferably a DNA molecule derived, for example, from a plasmid, bacteriophage or virus, into which a nucleic acid sequence may be inserted or cloned. Non-limiting examples of vectors include plasmids, phages, cosmids, phagemids, yeast artificial chromosomes (YAC), bacterial artificial chromosomes (BAC), human artificial chromosomes (HAC), viral vectors such as adenoviral vectors or retroviral vectors, and other DNA sequences which are conventionally used in genetic engineering and/or able to convey a desired DNA sequence to a desired location within a host cell.

A vector preferably contains one or more restriction sites and may be capable of autonomous replication in a defined host cell including a target cell or tissue or a progenitor cell or tissue thereof, or be partially or entirely integrable with the genome of the defined host such that the cloned sequence is reproducible. Accordingly, the vector may be an autonomously replicating vector, i.e. a vector that exists as an extrachromosomal entity, the replication of which is independent of chromosomal replication, e.g. a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The choice of the vector will typically depend on the compatibility of the vector with the host cell into which the vector is to be introduced.

The vector may further comprise one or more nucleic acid sequences encoding selectable marker such as auxotrophic markers (e.g., LEU2, URA3, TRP 1 or HISS), detectable labels such as fluorescent or luminescent proteins (e.g., GFP, eGFP, DsRed, CFP), or protein conferring resistance to a chemical/toxic compound (e.g., MGMT gene conferring resistance to temozolomide). These markers can be used to select or detect host cells comprising the vector and can be easily chosen by the skilled person according to the host cell.

The vector of the invention is preferably a viral genome vector including any element required to establish the expression of the recombinant nucleic acid molecule of the invention in a host cell such as, for example, a promoter, an ITR, a ribosome binding element, terminator, enhancer, selection marker, intron, polyA signal, and/or origin of replication.

In some embodiments, the vector is a viral vector, such as vectors derived from Moloney murine leukemia virus vectors (MoMLV), MSCV, SFFV, MPSV or SNV, lentiviral vectors (e.g. derived from human immunodeficiency virus (HIV), simian immunodeficiency virus (SIV), feline immunodeficiency virus (FIV), bovine immunodeficiency virus (BIV) or equine infectious anemia virus (EIAV)), adenoviral (Ad) vectors, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors.

In particular embodiments, the vector is a retroviral vector, preferably a lentiviral vector or a non-pathogenic parvovirus.

As known in the art, depending on the specific viral vector considered for use, suitable sequences should be introduced in the vector of the invention for obtaining a functional viral vector, such as AAV ITRs for an AAV vector, or LTRs for lentiviral vectors.

In preferred embodiments, the vector is an AAV vector.

The human parvovirus Adeno-Associated Virus (AAV) is a dependovirus that is naturally defective for replication which is able to integrate into the genome of the infected cell to establish a latent infection. The last property appears to be unique among mammalian viruses because the integration occurs at a specific site in the human genome, called AAVS1, located on chromosome 19 (19q13.3-qter). Therefore AAV has arisen considerable interest as a potential vector for human gene therapy. Among the favourable properties of the virus are its lack of association with any human disease, its ability to infect both dividing and non-dividing cells, and the wide range of cell lines derived from different tissues that can be infected.

As used herein, the term "AAV vector" refers to a polynucleotide vector comprising one or more heterologous sequences (i.e., nucleic acid sequence not of AAV origin) that are flanked by at least one AAV inverted terminal repeat sequence (ITR), preferably two ITRs. Such AAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins).

An "inverted terminal repeat" or "ITR" sequence is a term well understood in the art and refers to relatively short sequences found at the termini of viral genomes which are in opposite orientation. An "AAV inverted terminal repeat (ITR)" sequence is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C and D regions), allowing intra-strand base-pairing to occur within this portion of the ITR. AAV ITRs for use in the vectors of the invention may have a wild-type nucleotide sequence or may be altered by the insertion, deletion or substitution. The serotype of the inverted terminal repeats (ITRs) of the AAV vector may be selected from any known human or nonhuman AAV serotype.

Multiple serotypes of adeno-associated virus (AAV), including 12 human serotypes and more than 100 serotypes from nonhuman primates have now been identified (Howarth al., 2010, Cell Biol Toxicol 26: 1-10). Among these serotypes, human serotype 2 was the first AAV developed as a gene transfer vector. Other currently used AAV serotypes include, but are not limited to, AAV1, AAV3, AAV4, AAV5, AAV6, AAV7, AAV8, AAVrh8, AAV9, AAV10, AAVrh10, AAV11, AAV12, AAVrh74 and AAVdj, etc. In addition, non-natural engineered variants and chimeric AAV can also be useful.

Preferably, the vector of the present invention is an AAV6 vector.

When an AAV vector is incorporated into a larger poly-nucleotide (e.g., in a chromosome or in another vector such as a plasmid used for cloning or transfection), then the AAV vector may be referred to as a "pro-vector" which can be "rescued" by replication and encapsidation in the presence of AAV packaging functions and suitable helper functions. The AAV vector of the invention can be in any of a number of forms, including, but not limited to, plasmids, linear artificial chromosomes, complexed with lipids, encapsulated within liposomes, and encapsidated in a viral particle, e.g., an AAV particle.

The recombinant nucleic acid molecule or expression cassette of the invention may be introduced into the vector by any method known by the skilled person.

All the embodiments of the recombinant nucleic acid molecule and expression cassette of the invention are also contemplated in this aspect.

The vector of the invention may be packaged into a virus capsid to generate a "viral particle". Thus, in a further aspect, the present invention also relates to a viral particle comprising a vector of the invention.

In a particular embodiment, the vector is an AAV vector and is packaged into an AAV-derived capsid to generate an "adeno-associated viral particle" or "AAV particle". Thus, used herein, the term "AAV particle" refers to a viral particle composed of at least one AAV capsid protein and an encapsidated AAV vector genome.

The capsid serotype determines the tropism range of the AAV particle.

The capsid serotype may be selected from human or non-human serotypes previous identified or from non-natural engineered variants and chimeric AAV capsids. In particular, the capsid proteins may be variants comprising one or more amino acid substitutions enhancing transduction efficiency.

Different AAV serotypes are used to optimize transduction of particular target cells or to target specific cell types within a particular target tissue. An AAV particle can comprise viral proteins and viral nucleic acids of the same serotype or any natural or artificial sequence variant of AAV. For example, the AAV particle may comprise AAV6 capsid proteins and at least one, preferably two, AAV6 ITR. Any combination of AAV serotypes for production of an AAV particle is provided herein as if each combination had been expressly stated herein.

In preferred embodiment, the AAV particle comprises an AAV6-derived capsid.

AAV viruses may be engineered using conventional molecular biology techniques, making it possible to optimize these particles for cell specific delivery of nucleic acid sequences, for minimizing immunogenicity, for tuning stability and particle lifetime, for efficient degradation, for accurate delivery to the nucleus.

Alternatively to using AAV natural serotypes, artificial AAV serotypes may be used in the context of the present invention, including, without limitation, AAV with a non-naturally occurring capsid protein. Such an artificial capsid may be generated by any suitable technique, using a selected AAV sequence (e.g., a fragment of a VP1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid or a mutated AAV capsid.

A chimeric capsid comprises VP capsid proteins derived from at least two different AAV serotypes or comprises at least one chimeric VP protein combining VP protein regions or domains derived from at least two AAV serotypes.

Capsid proteins may also be mutated, in particular to enhance transduction efficiency. Mutated AAV capsids may be obtained from capsid modifications inserted by error prone PCR and/or peptide insertion or by including one or several amino acids substitutions.

In addition, the genome vector (i.e. a vector of the invention) of the AAV particle may either be a single stranded or self-complementary double-stranded genome. Self-complementary double-stranded AAV vectors are generated by deleting the terminal resolution site (trs) from one of the AAV terminal repeats. These modified vectors, whose replicating genome is half the length of the wild type AAV genome have the tendency to package DNA dimers. In a preferred embodiment, the AAV particle implemented in the practice of the present invention has a single stranded genome.

Numerous methods are known in the art for production of viral particles, and in particular AAV particles, including transfection, stable cell line production, and infectious hybrid virus production systems which include adenovirus-AAV hybrids, herpesvirus-AAV hybrids (Conway, J E et al., (1997) Virology 71(11):8780-8789) and baculovirus-AAV hybrids).

AAV production cultures for the production of AAV virus particles all require; 1) suitable host cells, including, for example, human-derived cell lines such as HeLa, A549, or 293 cells, or insect-derived cell lines such as SF-9, in the case of baculovirus production systems; 2) suitable helper virus function, provided by wild-type or mutant adenovirus (such as temperature sensitive adenovirus), herpes virus, baculovirus, or a plasmid construct providing helper functions; 3) AAV rep and cap genes and gene products; 4) a nucleic acid of interest flanked by at least one AAV ITR sequences, e.g., a vector of the invention; and 5) suitable media and media components to support AAV production that are well-known in the art.

In practicing the invention, host cells for producing AAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293, A549 or HeLa cells. AAV particles are then purified and formulated using standard techniques known in the art.

All the embodiments of the recombinant nucleic acid molecule, the expression cassette or the vector of the invention are also contemplated in this aspect.

In another aspect, the present invention also relates to an isolated host cell comprising, transformed or transfected with, an expression cassette, vector or viral particle of the invention.

The host cell may comprise one or several recombinant nucleic acids, expression cassettes or vectors of the invention, identical or different.

In a particular embodiment, the host cell comprises a recombinant nucleic acid of the invention which includes a splice donor site at its 3' end, said splice donor site being compatible with a splice acceptor site in the genome of the host cell.

The term "host cell" also encompasses any progeny of a parent host cell that is not identical to the parent host cell due to mutations that occur during replication.

The term "cell" or "host cell" includes any cell that is suitable for expressing a recombinant nucleic acid molecule of the invention. Suitable host cells for expression of antibody-encoding vectors include prokaryotic or eukaryotic cells described herein.

For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, NJ, 2003), pp. 245-254, describing expression of antibody fragments in E. coli.) After expression, the antibody may be isolated from the bacterial cell lysate in a soluble fraction and can be further purified.

In addition to prokaryotes, eukaryotic microbes such as filamentous fungi or yeast are suitable expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22: 1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See, e.g., U.S. Pat. Nos. 5,959,177, 6,040, 498, 6,420,548, 7,125,978, and 6,417,429.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse Sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N. Y. Acad. Sci. 383:44-68 (1982); MRC 5 cells; and FS4 cells. Other useful mammalian host cell lines include Chinese hamster ovary (CHO) cells, including DHFR⁻ CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

In a particular embodiment, the host cell is selected from mycobacteria cells, fungal cells, yeast cells, plant cells, insect cells, non-human animal cells, human cells, or cell fusions such as, for example, hybridomas. Preferably, the cell is selected from mammals. Preferably, the cell is selected from human, primate, rabbit or rodents (e.g., mice, rats, hamsters, guinea pigs) cells. More preferably, the cell is selected from human and mouse cells. Even more preferably, the cell is a human cell. In preferred embodiments, human embryonic stem cells are excluded.

In preferred embodiments, the cell is a B cell, preferably a human or mouse B cell, more preferably a human B cell.

The host cell, preferably the non-human cell, may also be a totipotent, pluripotent, or adult stem cell, a zygote, or a somatic cell. In an embodiment, the host cell is an embryonic stem cell, preferably a non-human embryonic stem cell, more preferably a mouse embryonic stem cell.

The expression cassette or vector of the invention may be transferred into host cells using any known technique including, but being not limited to, calcium phosphate-DNA precipitation, DEAE-Dextran transfection, electroporation, microinjection, biolistic, lipofection, or viral infection, and may be maintained in the host cell in an ectopic form or may be integrated into the genome.

In preferred embodiments, the expression cassette or vector of the invention is transferred into the host cell by viral infection, preferably using a viral particle of the invention, more preferably using an AAV particle of the invention.

All the embodiments of the recombinant nucleic acid molecule, the expression cassette, the vector or the viral particle of the invention are also contemplated in this aspect.

In another aspect, the present invention further relates to a transgenic organism, preferably a non-human transgenic organism, comprising at least one host cell of the invention. The invention also relates to a method of generating a transgenic organism comprising at least one transgenic host cell of the invention.

All embodiments of the recombinant nucleic acid molecule, the expression cassette, the vector, the viral particle and the host cell of the invention are also contemplated in this aspect.

In particular, the organism may be a non-human animal, such as primates (e.g., non-human primates such as monkeys), rabbits, or rodents (e.g., mice, rats, hamsters, guinea pigs). Preferably, the transgenic organism is a non-human mammal More preferably, the transgenic organism is a mouse.

Methods of generating transgenic organisms, in particular transgenic mice are well-known by the skilled person. It should be understood that any of these methods can be used to practice the invention and that the methods disclosed herein are non-limitative.

In particular, the method of generating a transgenic organism may comprise
introducing an expression cassette or a vector of the invention in a non-human embryonic stem cell,
obtaining a transgenic embryonic stem cell wherein the recombinant nucleic acid molecule of the invention is inserted into the genome, preferably by homologous recombination,
injecting said transgenic embryonic stem cell into a blastocyst of a non-human animal to form chimeras, and
reimplanting said injected blastocyst into a foster mother.
Embryonic stem (ES) cell are typically obtained from pre-implantation embryos cultured in vitro. Preferably, the cassette or vector of the invention is transfected into said ES cell by electroporation. The ES cells are cultured and prepared for transfection using methods known in the related art. The ES cells that will be transfected with the cassette or vector of the invention are derived from embryo or blastocyst of the same species as the developing embryo or blastocyst into which they are to be introduced. ES cells are typically selected for their ability to integrate into the inner cell mass and contribute to the germ line of an individual when introduced into the animal in an embryo at the blastocyst stage of development. In one embodiment, the ES cells are isolated from the mouse blastocysts.

After transfection into the ES cells, the recombinant nucleic acid molecule of the invention integrates with the genomic DNA of the cell in order to produce an antibody of the invention as defined below.

After transfection, the ES cells are cultured under suitable condition to detect transfected cells. For example, when the cassette or vector comprises a marker gene, e.g. an antibiotic resistant marker, e.g. neomycin resistant gene, the cells are cultured in that antibiotic. The DNA and/or protein expression of the surviving ES cells may be analyzed using Southern Blot technology in order to verify the proper integration of the cassette.

The selected ES cells are then injected into a blastocyst of a non-human animal to form chimeras. The non-human animal is preferably a mouse, a hamster, a rat or a rabbit. More preferably, the non-human animal is a mouse.

In particular, the ES cells may be inserted into an early embryo using microinjection. The injected blastocysts are re-implanted into a foster mother. When the progenies are born, they are screened for the presence of the recombinant nucleic acid molecule, expression cassette or vector of the invention, e.g. using Southern Blot and/or PCR technique. The heterozygotes are identified and are then crossed with each other to generate homozygous animals.

In another embodiment, the method of generating a transgenic organism may comprise
introducing in a non-human fertilized egg (i) an expression cassette or vector of the invention and (ii) a nuclease system used to target the cassette or vector at the correct locus by homologous recombination,
obtaining a transgenic fertilized egg wherein the expression cassette or vector of the invention is inserted into the genome by homologous recombination, and
reimplanting said injected fertilized egg into a foster mother.
The nuclease system used to target the cassette or vector at the correct locus may be any suitable system known by the skilled person, such as systems involving ZFN, TALE or CRISPR/Cas9 nucleases.

Preferably, the nuclease system is a CRISPR/Cas9 system. To use Cas9 to modify genomic sequences, the protein can be delivered directly to a cell. Alternatively, an mRNA that encodes Cas9 can be delivered to a cell, or a gene that provides for expression of an mRNA that encodes Cas9 can be delivered to a cell. In addition, either target specific crRNA and a tracrRNA or target specific gRNA(s) can be delivered to the cell (these RNAs can alternatively be produced by a gene constructed to express these RNAs). Selection of target sites and designed of crRNA/gRNA are well known in the art.

The present invention also provides cells or tissues, including immortalized cell lines and primary cells or tissues, derived from the transgenic non-human animal of the invention and its progeny, in particular cells or tissues producing an antibody of the invention such as hybridomas or myelomas.

In another aspect, the present invention relates to an antibody comprising
an immunoglobulin heavy chain variable region ($V_H$),
an immunoglobulin light chain variable region ($V_L$),
an immunoglobulin light chain constant region ($C_L$),
an immunoglobulin heavy chain constant region ($C_H$), and
two sequences encoding peptide linkers (PL1 and PL2),
wherein $V_H$ is fused to $V_L$ through PL1 and $C_L$ is fused to $C_H$ through PL2.
PL1 and PL2 may be identical or different.
In particular, the antibody of the invention may be any antibody obtained via the expression of the coding sequences of the recombinant nucleic acid molecule of the invention.

All embodiments of the recombinant nucleic acid molecule, the expression cassette, the vector, the viral particle, the host cell and the transgenic animal of the invention are also contemplated in this aspect.

The term "antibody" herein is used in the broadest sense and specifically covers monoclonal antibodies (including full length monoclonal antibodies), polyclonal antibodies, multispecific antibodies (e.g., bispecific antibodies), antibody fragments, and derivatives thereof, as long as they comprise a chain comprising $V_H$, $V_L$, $C_L$, $C_H$, PL1, PL2, $V_H$ being fused to $V_L$ through PL1 and $C_L$ being fused to $C_H$ through PL2.

The antibody of the invention may be a single chain antibody comprising only one chain comprising $V_H$, $V_L$, $C_L$, $C_H$, PL1 and PL2. Alternatively, the antibody of the invention may comprise at least two chains comprising $V_H$, $V_L$, $C_L$, $C_H$, PL1 and PL2 and as defined above, said chains being preferably linked together via disulfure bridges.

In a particular embodiment, the antibody of the invention comprises two chains linked via one or several disulfure bridges, each chain comprising an immunoglobulin heavy chain variable region ($V_H$), an immunoglobulin light chain variable region ($V_L$), an immunoglobulin light chain constant region ($C_L$), an immunoglobulin heavy chain constant region ($C_H$), and two sequences encoding peptide linkers (PL1 and PL2), wherein $V_H$ is fused to $V_L$ through PL1 and $C_L$ is fused to $C_H$ through PL2.

In some embodiments, the antibody may be part of a larger fusion molecule, formed by covalent or non-covalent association of the antibody with one or more other proteins or peptides. In particular, the antibody of the invention may further comprise additional antibody domains, e.g. additional heavy and light chain domains.

In some embodiments, the antibody is a full length antibody. The term "full length antibody", as used herein, refers to an antibody having a structure substantially similar to a native antibody structure, not antibody fragments as defined below. The terms particularly refer to an antibody with heavy chains that contain an Fc region. In preferred embodiments, the antibody in a full-length IgG antibody selected from IgG1, IgG2, IgG3 and IgG4, preferably a full length IgG1 antibody. However, any other immunoglobulin class can be used.

In some other embodiments, the antibody is an antibody fragment. As used herein, the term "antibody fragment" refers to a portion of a full length antibody, preferably fragment comprising the variable domain of the heavy chain, the linker PL1, the light chain, the linker P2 and at least a fragment of the N-terminus of the constant heavy chain. Antibody fragments are preferably selected from the group consisting of Fab, Fab', F(ab)₂, F(ab')₂ and F(ab)₃.

Antibody fragments can be made by various techniques, including but not limited to proteolytic digestion of intact antibody, well-known by the skilled person, as well as recombinant techniques described herein. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

By "Fab", "Fab fragment" or "Fab region" as used herein is meant the polypeptide that comprises the $V_H$, CH1, $V_L$, and $C_L$ immunoglobulin domains. Fab may refer to this region in isolation or this region in the context of a poly-peptide as described herein.

Fab' fragments differ from Fab fragments by the addition of a few residues at the carboxy terminus of the heavy chain CH1 domain including one or more cysteines from the antibody hinge region. F(ab')2 antibody fragments originally were produced as pairs of Fab' fragments which have hinge cysteines between them. Other chemical couplings of anti-body fragments are also known.

The term "antibody derivative", as used herein, refers to an antibody provided herein, e.g. a full-length antibody or a fragment of an antibody, wherein one or more of the amino acids are chemically modified, e.g. by alkylation, PEGy-lation, acylation, ester or amide formation or the like. In particular, this term may refer to an antibody provided herein that is further modified to contain additional nonproteina-ceous moieties that are known in the art and readily avail-able. The moieties suitable for derivatization of the antibody include but are not limited to water soluble polymers. Examples of water soluble polymers include, but are not limited to, PEG, copolymers of ethylene glycol/propylene glycol, carboxymethylcellulose, dextran and polyvinyl alco-hol.

The derivative may also be an immunoconjugate com-prising an antibody of the invention conjugated to one or more heterologous molecule(s), including but not limited to a cytotoxic agent, a detectable moiety such as a fluorescent moiety, a diagnostic radioisotope or an imaging agent; or to a solid support, such as agarose beads or the like. Examples of cytotoxic agents include, but are not limited to chemo-therapeutic agents or drugs, growth inhibitory agents, toxins (e.g., protein toxins, enzymatically active toxins of bacterial, fungal, plant, or animal origin, or fragments thereof), or radioactive isotopes. Conjugates of an antibody and cyto-toxic agent may be made using a variety of bifunctional protein coupling agents well known by the skilled person. The linker may be a "cleavable linker" facilitating release of a cytotoxic drug in the cell. For example, an acid-labile linker, peptidase-sensitive linker, photolabile linker, dim-ethyl linker or disulfide-containing linker (Chari et al., Cancer Res. 52: 127-131 (1992)) may be used.

The antibody of the invention may comprise a functional Fc region, a native sequence Fc region or a variant Fc region.

A "functional Fc region" possesses an effector function of a native sequence Fc region. Exemplary "effector functions" include C1q binding; Cell Dependent Cytotoxicity (CDC); Fc receptor binding; Antibody Dependent Cell Cytotoxicity (ADCC), phagocytosis, Antibody Dependent Cell Phagocy-tosis (ADCP), down regulation of cell surface receptors, etc. Such effector functions generally require the Fc region to be combined with a binding domain (e.g., an antibody variable domain) and can be assessed using various well known assays.

A "native sequence Fc region" comprises an amino acid sequence identical to the amino acid sequence of an Fc region found in nature, preferably a native sequence human Fc region.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most pref-erably at least about 90% sequence identity therewith, more preferably at least about 95% sequence identity therewith. In some embodiments, the antibody provided herein is a mul-tispecific antibody, e.g. a bispecific antibody. Multispecific antibodies are monoclonal antibodies that have binding specificities for at least two different sites.

Multispecific antibodies of the invention may be obtained through the recombinant co-expression in a host cell of two recombinant nucleic acid molecule of the invention leading to two single chain antibodies of the invention. These chains naturally associate together via disulfure bridges to form a multispecific antibody comprising at least two light chains and at least two heavy chains, the variable domains of said chains recognizing at least two different epitopes.

In some embodiments, the antibody is a purified antibody. A "purified" antibody is one which has been separated from a component of its production environment, preferably separated from its producing cell and/or from other antibodies. In particular, the antibody may be purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g. Flatman et al., J. Chromatogr. B 848:79-87 (2007). The antibody may, for example, be purified from the culture medium comprising the host cell expressing a recombinant nucleic acid molecule of the invention.

Depending on the method of producing the antibody of the invention or the application, the antibody of the invention may be a polyclonal or monoclonal antibody. Preferably, the antibody is a monoclonal antibody. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The monoclonal antibody may be made by any method known by the skilled person.

The antibody of the invention may be a chimeric, humanized or human antibody.

"Chimeric" antibodies are antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Morrison et al., Proc. Natl. Acad Sci. USA 81:6851-6855 (1984)). Preferably, at least a portion of the framework of the antibody is a human consensus framework sequence.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also comprises at least a portion of an immunoglobulin constant region (Fc), typically that of a human immunoglobulin (Jones et al., Nature 321:522-525 (1986); Reichmann et al., Nature 332:323.329 (1988); and Presta, Curr Op. Struct. Biol. 2:593-596 (1992)). Additional framework region modifications may be made within the human framework sequences. Humanized antibodies thus may also comprise residues that are not found in either the recipient antibody or the donor antibody. Such amino acid modifications may be made to further refine antibody function and/or increased the humanization process. The "humanness" of an antibody may be measured using the T20 score analyzer to quantify the humanness of the variable regions of antibodies as described in Gao S H, Huang K, Tu H, Adler A S. BMC Biotechnology. 2013: 13:55. A "human antibody" or "fully human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

In preferred embodiments, the antibody of the invention is a monoclonal antibody, preferably a human monoclonal antibody.

The antibody of the invention is preferably a therapeutic antibody. The therapeutic antibody may be useful for the treatment of any disease, such as cancer, inflammatory diseases, infectious diseases or auto-immune diseases.

In particular, the antibody of the invention may comprise the variable and/or constant regions of a therapeutic antibody, preferably of an approved (e.g. EMA or FDA approved) therapeutic antibody. In a particular embodiment, the antibody of the invention comprises the variable and constant regions of a therapeutic antibody, preferably of an approved therapeutic antibody. Examples of such therapeutic antibodies include, but are not limited to, abciximab, adalimumab, alemtuzumab, alirocumab, atezolizumab, avelumab, basiliximab, belimumab, bevacizumab, bezlotoxumab, blinatumomab, brentuximab, brodalumab, canakinumab, capromab, cetuximab, daclizumab, daratumumab, denosumab, dinutuximab, dupilumab, durvalumab, eculizumab, elotuzumab, evolocumab, golimumab, ibritumomab, idarucizumab, infliximab, ipilimumab, ixekizumab, mepolizumab, natalizumab, necitumumab, nivolumab, obiltoxaximab, obinutuzumab, ocrelizumab, ofatumumab, olaratumab, omalizumab, palivizumab, panitumumab, pembrolizumab, pertuzumab, ramucirumab, ranibizumab, reslizumab, secukinumab, siltuximab, tocilizumab, ustekinumab, vedolizumab, sarilumab, rituximab, guselkumab, inotuzumab, adalimumab, gemtuzumab, bevacizumab, benralizumab, emicizuma and trastuzumab.

The present invention also concerns a method of producing an antibody of the invention, comprising providing a host cell or a transgenic organism of the invention, culturing said a host cell or allowing said organism to grow, under conditions suitable for expression of the antibody, and optionally recovering the antibody from the host cell culture or from a sample of said organism. Optionally, the recovered antibody may be further purified. Suitable media, culture conditions and production method are well-known by the skilled person and can be easily chosen according to the host cell and the antibody to be produced. Preferably, the host cell or the transgenic organism is non-human.

In another aspect, the present invention further relates to a pharmaceutical composition comprising a recombinant nucleic acid molecule, an expression cassette, a vector, a viral particle, a host cell or an antibody of the invention, and a pharmaceutical acceptable excipient. The composition may comprise one or several recombinant nucleic acid molecules, one or several expression cassettes, one or several vectors, one or several viral particles, one or several host cells and/or one or several antibodies of the invention.

As used herein, the term "pharmaceutical formulation" or "pharmaceutical composition" refers to a preparation which is in such form as to permit the biological activity of the active ingredient to be effective, and which contains no additional components which are unacceptably toxic to a subject to which the formulation would be administered. Preferably, such formulations are sterile, i.e. aseptic or free from all living microorganisms and their spores.

As used herein, the term "pharmaceutically acceptable" means approved by a regulatory agency or recognized pharmacopeia such as European Pharmacopeia, for use in animals and/or humans. The term "excipient" refers to a diluent, adjuvant, carrier, or vehicle with which the therapeutic agent is administered.

Acceptable carriers, excipients, or stabilizers are nontoxic to recipients at the dosages and concentrations employed, and include, but are not limited to, buffering agents, stabilizing agents, preservatives, isotonifiers, non-ionic detergents, antioxidants and other miscellaneous additives.

As is well known in the art, pharmaceutically acceptable excipients are relatively inert substances that facilitate administration of a pharmacologically effective substance and can be supplied as liquid solutions or suspensions, as emulsions, or as solid forms suitable for dissolution or suspension in liquid prior to use. For example, an excipient can give form or consistency, or act as a diluent. Suitable excipients include but are not limited to stabilizing agents, wetting and emulsifying agents, salts for varying osmolality, encapsulating agents, pH buffering substances, and buffers. Such excipients include any pharmaceutical agent suitable for direct delivery to the eye which may be administered without undue toxicity. Pharmaceutically acceptable excipients include, but are not limited to, sorbitol, any of the various tween compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences, 15th Edition.

The form of the pharmaceutical compositions, the route of administration, the dosage and the regimen depend upon the condition to be treated, the severity of the illness, the age, weight, and sex of the patient, etc.

The doses used for the administration can be adapted as a function of various parameters, and in particular as a function of the mode of administration used, of the relevant pathology, or alternatively of the desired duration of treatment.

The pharmaceutical compositions of the invention can be formulated for a topical, oral, parenteral, intranasal, intravenous, intramuscular, subcutaneous or intraocular administration and the like.

Preferably, the pharmaceutical formulation is a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

Sterile injectable solutions may be prepared by incorporating the active compounds in the required amount in the appropriate solvent with various of the other ingredients enumerated above, as required, followed by filtered sterilization. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In addition to the compositions formulated for parenteral administration, such as intravenous or intramuscular injection, other pharmaceutically acceptable forms include, e.g. tablets or other solids for oral administration; time release capsules; and any other form currently used.

The pharmaceutical composition may further comprise one or several additional active compounds. Examples of additional active compounds include, but are not limited to, chemotherapeutic drug, antibiotics, antiparasitic agents, antifungal agents or antiviral agents.

All the embodiments of the recombinant nucleic acid molecule, the expression cassette, the vector, the viral particle, the host cell and the antibody of the invention are also contemplated in this aspect.

The present invention further relates to a recombinant nucleic acid molecule, an expression cassette, a vector, a viral particle, a host cell, an antibody or a pharmaceutical composition of the invention for use in the prevention or treatment of a disease.

The present invention relates to the use of a recombinant nucleic acid molecule, an expression cassette, a vector, a viral particle, a host cell, an antibody or a pharmaceutical composition of the invention as a medicament for the treatment of a disease. The invention also relates to the use of a recombinant nucleic acid molecule, an expression cassette, a vector, a viral particle, a host cell or an antibody of the invention for the manufacture or preparation of a medicament.

In particular, the present invention relates to a method of treating a disease in a subject, comprising administering to said subject an effective amount of a recombinant nucleic acid molecule, an expression cassette, a vector, a viral particle, a host cell, an antibody or a pharmaceutical composition of the invention.

As used herein, the term "subject" or "patient" refers to a mammal, preferably a human being.

The disease may be any disease which can be treated, prevented or alleviated through the action of an antibody, in particular an antibody of the invention. Examples of such diseases include, but are not limited to, cancer, infectious diseases, auto-immune diseases and inflammatory diseases.

All the embodiments of the recombinant nucleic acid molecule, the expression cassette, the vector, the viral particle, the host cell, the antibody and the pharmaceutical composition of the invention are also contemplated in this aspect.

The present invention further relates to a recombinant nucleic acid molecule, an expression cassette, a vector, a viral particle, a host cell, an antibody or a pharmaceutical composition of the invention, preferably an antibody of the invention, for use in a method of diagnosis or detection of a disease.

The disease to be diagnosed or detected depends on the antibody.

The method may comprise contacting the biological sample with an antibody of the invention under conditions permissive for binding of the antibody to its antigen, if present in the sample, and detecting whether a complex is formed between the antibody and its antigen. Such method may be an in vitro or in vivo method. The term "detecting" as used herein encompasses quantitative or qualitative detection.

In preferred embodiments, the antibody of the invention used in diagnostic methods is labelled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

The present invention further relates to a kit for diagnosis or detection of a disease comprising a recombinant nucleic acid molecule, an expression cassette, a vector, a viral particle, a host cell, an antibody or a pharmaceutical composition of the invention, and optionally a leaflet providing guidelines to use such a kit. The kit of the invention may further comprise one or several reagents required to detect the complex of the antibody of the invention with its antigen. The present invention further relates to the use of a kit of the invention to diagnose or detect a disease.

As used in this specification, the term "about" refers to a range of values±10% of the specified value, more preferably a range of values±5% of the specified value. For instance, "about 1" means from 0.9 to 1.1 when 10% is considered and from 0.95 to 1.05 when 5% is considered.

As used herein, the verb "to comprise" is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are given for purposes of illustration and not by way of limitation.

EXAMPLES

Material and Method

Construction of an Anti-CD20 scFull-Ig

Gene synthesis reaction was used to create a fully synthetic cassette encoding an anti-CD20 scFull-Ig (single chain full length Ig). Variable domains were based on the rituximab sequence. In order to obtain a single-chain Fab fragment, we designed an original strategy by which:

full-length $V_H$,$DJ_H$ and $V_k J_k$ were linked by a 18-residue linker (Whitlow 218 linker; GSTSGSGKPGSGEG-STKG (SEQ ID NO: 1)

24 this was followed by $C_k$ and a γ heavy chain CH1 domain again ligated by the very same 18-residue linker sequence.

This sequence encoding a single chain "Fab" domain was then followed by the $C_H2$ and $C_H3$ sequences and a polyadenylation site. Since optimal expression of Ig sequences is favored by introns, we included the natural first intron [leader exon-$V_H$ exon] upstream of the $V_H$ sequence, to conserve the $V_H$ genomic structure with exon 1 and 2, according to germline sequence. Additionally, a $V_H$ promoter sequence was inserted upstream of the construction.

Finally, the construct was cloned into the pCDNA3.1(+) vector, which contains a neomycin gene resistance for selection, at the HindIII and EcoRI sites.

Production

CHO and 293 cells were transfected with the plasmid vector by Macsfectin reagent, and selected with 0.5 to 1 mg/mL G418 complemented media the day after transfection. After 3-4 weeks, supernatants were screened for expression by an enzyme-linked immunosorbent assay, and by flow cytometry. Supernatant was eventually concentrated by centrifugation on a Vivaspin disposal with a 10-kDa cut-off.

Characterization

For ELISA, the scFull-Ig was captured by polyclonal anti-human Fc-specific antibodies, and detected by HRP-conjugated anti-human IgG (H+L) antibodies (both from Sigma Aldrich).

For flow cytometry, 100 000 cells expressing the CD20 membrane antigen (or negative control cells) were incubated with 50 μL of supernatant during 30 min at 2-8° C. After 3 washes with cold PBS-1% SAB, 10 μL of diluted anti-human IgG (H+L)-Dylight 650 was added to the cell suspension. Subsequently a 20-min incubation at 2-8° C., cells were washed again 3 times and finally re-suspended with 300 μl of buffer. Propidium iodide was added just before reading for exclude dead cells. 10 000 events gated on live cells were recorded on FACS Calibur cytometer.

Results

FIG. 1: Schematic diagram of the scFull-Ig strategy.

Figure 2:
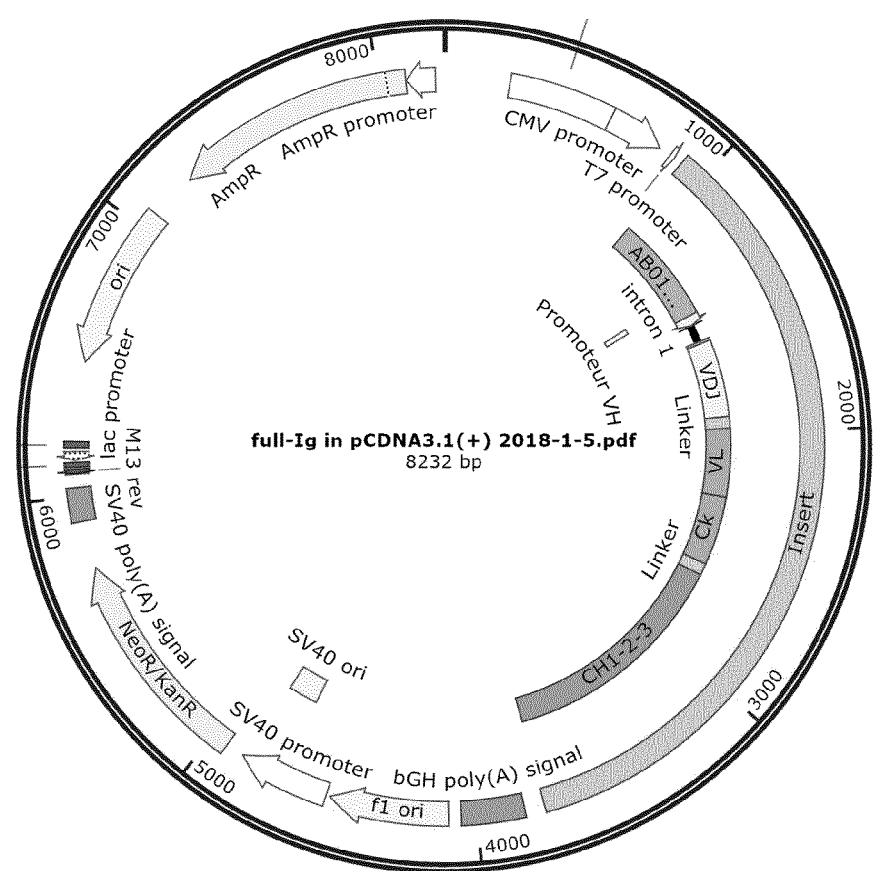
FIG. 2: The VDJ sequence of the rituximab was linked to the VJ sequence by the Whitlow 218 linker. To optimize the transcription, intronic structure was conserved between the first and the second exon coding the variable heavy domain. Constant kappa sequence was linked to the constant heavy chain by the same Whitlow 218 linker. Synthesis of this sequence was ordered from Genecust Company, and inserted in a pCDNA3.1 (+) vector.

FIG. 2: Map of the plasmid constructed for anti-CD20 scFull-Ig expression. Construction was inserted at the HindIII and EcoRI sites into a pCDNA3.1(+) vector.

Figure 3:
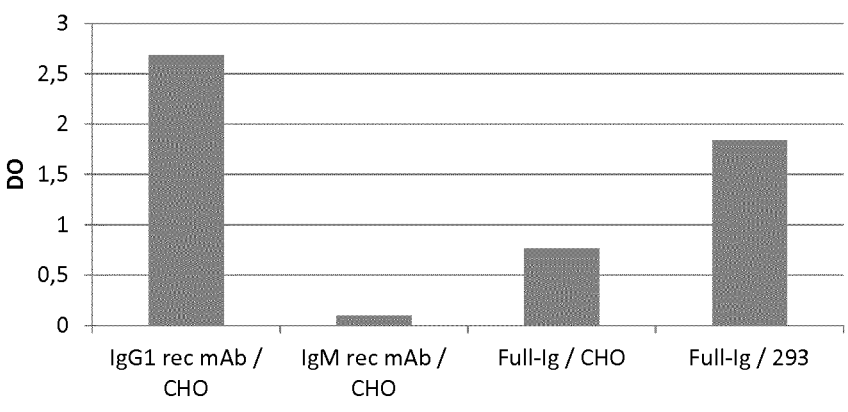
FIG. 3: Supernatant of transfected CHO or HEK 293 cell line were analyzed by ELISA method. IgG molecules in supernatant were trapped by anti-Fc polyclonal antibody coated on a 96 plates. Detection was realized by addition of HRP-coupled anti-IgG (H+L) polyclonal antibody. IgG1 recombinant protein was used as positive control whereas negative control was an IgM-class recombinant molecule.

FIG. 3: Detection of recombinant mAb in raw supernatant by ELISA. Supernatants from transfected cells were collected and analyzed by ELISA. Recombinant IgG1 and IgM mAb were used as, respectively, positive and negative control. As expected, scFull-Ig were detected both in CHO and 293 transfected cell line supernatant.

Figure 4A:
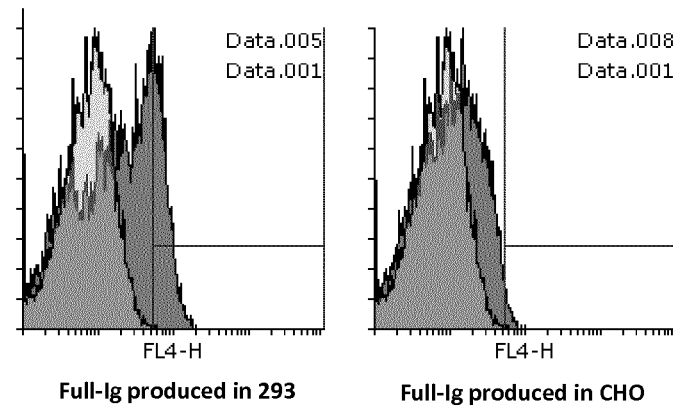
FIG. 4: Staining of target cells with scFull-Ig supernatant. 4A) Flow cytometry profile: Detection of scFull-Ig anti-CD20 on a positive CD20 cell line (SUDHL4 and DOHH), or a negative control: DOHH KOCD20, disrupted for CD20 expression). SUDHL4 cell line was incubated with 50 μL of supernatant at 2-8° C. during 30 min. After washes, fluorescent polyclonal anti-hIgG(H+L) antibody was incubated 20 min at 2-8° C. Cells were washes before flow analysis on a FACSCalibur cytometer. Geometric mean of fluorescence was measured on different cell lines (SUDHL4, DOHH2 and DOHH2 KO CD20), after incubation with diluted supernatant were plotted on the right histogram (4B).
Figure 4A:
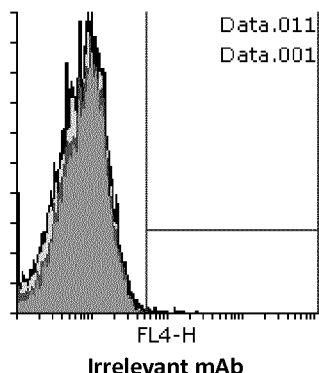
Figure 4B:
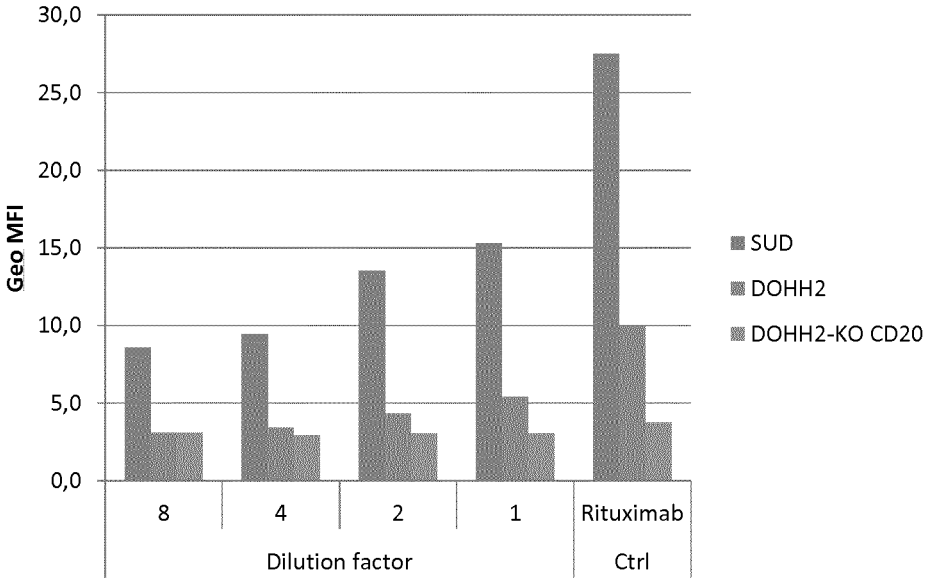

FIG. 4: Staining of target cells with scFull-Ig supernatant. To ensure functionality of the scFull-Ig structure, different cells targets were incubated with different batches or dilutions of raw supernatant. 4A, typical staining observed on SUD cell line with the different raw supernatant tested. 4B, geometric mean fluorescent measured on positive (SUD and DOHH2) or negative (DOHH2-KO CD20) CD20 cell line. Rituximab was used as positive control.

The invention claimed is:

1. A recombinant nucleic acid molecule comprising:
a sequence encoding an immunoglobulin heavy chain variable region ($V_H$),
a sequence encoding an immunoglobulin light chain variable region ($V_L$),
a sequence encoding a light chain constant region ($C_L$),
two sequences encoding peptide linkers (PL1 and PL2), wherein the peptide linkers PL1 and PL2 comprise SEQ ID NOs: 1, 3, 4, 5, 6, or 7;
a donor splice site, wherein the donor splice site is a donor splice site for junction with a CH1 domain of constant immunoglobulin heavy genes, and
wherein the nucleic acid encodes a molecule comprising the following structure:
$V_H$-PL1-$V_L$-$C_L$-PL2-donor splice site,
wherein PL1 and PL2 are identical or different, and
wherein the nucleic acid molecule is integrated between the joining region (JH) genes and the constant region ($C_H$) genes of immunoglobulin heavy chains in the genome of a host cell, wherein the host cell is a mouse B cell or a human B cell, thereby encoding a full-length single chain immunoglobulin comprising $V_H$-PL1-$V_L$-$C_L$-PL2-$C_H$ wherein $V_H$-PL1-$C_L$-PL2 are encoded by the recombinant nucleic acid molecule and $C_H$ is encoded by the host cell genome.

2. The recombinant nucleic acid molecule of claim 1, wherein PL1 and PL2 comprise SEQ ID NO: 1 or 4.

3. The recombinant nucleic acid molecule of claim 2, wherein PL1 and PL2 are different and comprise SEQ ID NO: 1 or SEQ ID NO: 4.

4. An expression cassette comprising the recombinant nucleic acid molecule of claim 1 operably linked to one or more control sequences that direct the expression of said nucleic acid in a suitable host cell under conditions compatible with the control sequences.

5. A vector comprising the expression cassette of claim 4.

6. The vector of claim 5, said vector being a viral vector.

7. The vector of claim 6, said vector being an adeno-associated viral (AAV) vector.

8. A viral particle comprising the vector of claim 5.

9. An isolated cell wherein the genome of said isolated cell comprises the recombinant nucleic acid molecule of claim 1 integrated into an immunoglobulin heavy locus between the joining region (JH) genes and the constant region (CH) genes of immunoglobulin heavy chains, wherein the isolated cell is a mouse B cell or a human B cell.

10. A method of producing a full-length single chain antibody comprising providing the cell of claim 9 that expresses a full-length single chain antibody, and recovering said full-length single chain antibody from cell culture.

* * * * *

SEQUENCE LISTING

<160> NUMBER OF SEQ ID NOS: 7

<210> SEQ ID NO 1

```
<211> LENGTH: 18
<212> TYPE: PRT
<213> ORGANISM: Artificial Sequence
<220> FEATURE:
<223> OTHER INFORMATION: Whitlow 218 linker

<400> SEQUENCE: 1

Gly Ser Thr Ser Gly Ser Gly Lys Pro Gly Ser Gly Glu Gly Ser Thr
1               5                   10                  15

Lys Gly

<210> SEQ ID NO 2
<211> LENGTH: 7
<212> TYPE: PRT
<213> ORGANISM: Artificial Sequence
<220> FEATURE:
<223> OTHER INFORMATION: Peptide linker PT1

<400> SEQUENCE: 2

Gly Gly Gly Ser Ala Ala Ala
1               5

<210> SEQ ID NO 3
<211> LENGTH: 10
<212> TYPE: PRT
<213> ORGANISM: Artificial Sequence
<220> FEATURE:
<223> OTHER INFORMATION: Peptide linker PT2

<400> SEQUENCE: 3

Gly Gly Gly Gly Ser Gly Gly Gly Gly Ser
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Peptide linker PT3

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 25
<212> TYPE: PRT
<213> ORGANISM: Artificial Sequence
<220> FEATURE:
<223> OTHER INFORMATION: Peptide linker L205

<400> SEQUENCE: 5

Ser Ser Ala Asp Asp Ala Lys Lys Asp Ala Ala Lys Lys Asp Asp Ala
1               5                   10                  15

Lys Lys Asp Asp Ala Lys Lys Asp Gly
            20                  25

<210> SEQ ID NO 6
<211> LENGTH: 21
<212> TYPE: PRT
<213> ORGANISM: Artificial Sequence
<220> FEATURE:
<223> OTHER INFORMATION: Peptide linker LLB18

<400> SEQUENCE: 6

Ser Pro Asn Gly Ala Ser His Ser Ser Ser Ala Ser Gln Thr Gly Ser
```

-continued

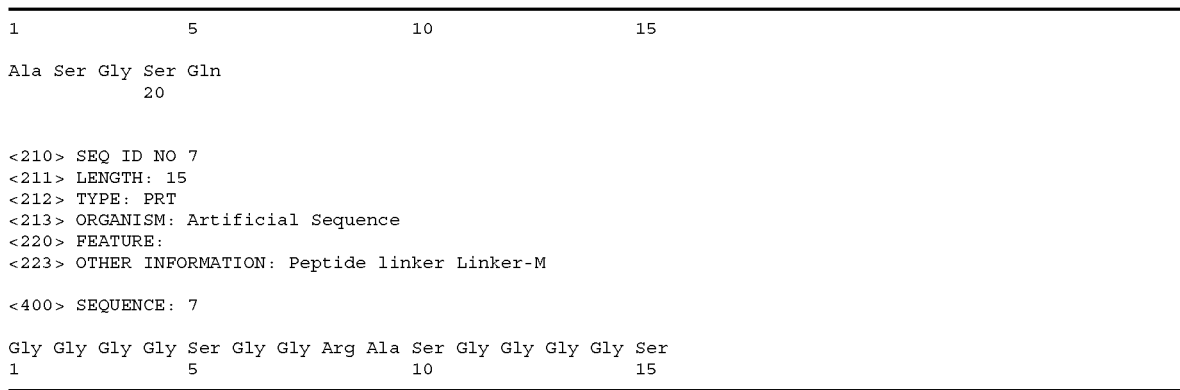

```
1              5              10             15

Ala Ser Gly Ser Gln
                 20

<210> SEQ ID NO 7
<211> LENGTH: 15
<212> TYPE: PRT
<213> ORGANISM: Artificial Sequence
<220> FEATURE:
<223> OTHER INFORMATION: Peptide linker Linker-M

<400> SEQUENCE: 7

Gly Gly Gly Gly Ser Gly Gly Arg Ala Ser Gly Gly Gly Gly Ser
1              5              10             15
```